United States Patent [19]

Snoke et al.

[11] Patent Number: 5,423,311

[45] Date of Patent: * Jun. 13, 1995

[54] CATHETER IMAGING APPARATUS

[75] Inventors: Phillip J. Snoke; Stephen C. Gamper, both of Atlanta; David S. Rowley, Smyrna; Bruce W. Copeland, Stone Mountain, all of Ga.

[73] Assignee: Catheter Imaging Systems, Altanta, Ga.

[*] Notice: The portion of the term of this patent subsequent to Aug. 30, 2011 has been disclaimed.

[21] Appl. No.: 963,431

[22] Filed: Oct. 19, 1992

Related U.S. Application Data

[63] Continuation-in-part of Ser. No. 908,403, Jul. 6, 1992, Pat. No. 5,342,299.

[51] Int. Cl.$^6$ .............................................. A61B 1/018
[52] U.S. Cl. ............................................. 128/6; 609/95
[58] Field of Search ........................ 358/98; 128/4, 6; 604/95; 385/117, 118

[56] References Cited

U.S. PATENT DOCUMENTS

| | | | |
|---|---|---|---|
| 3,831,017 | 8/1974 | Aver | 128/6 X |
| 4,279,245 | 7/1981 | Takagi et al. | 128/4 |
| 4,344,092 | 8/1982 | Miller | 358/217 |
| 4,413,278 | 11/1983 | Feinbloom | 358/98 |
| 4,433,675 | 2/1984 | Konoshima | 128/6 |
| 4,475,539 | 10/1984 | Konomura | 128/6 |
| 4,539,586 | 9/1985 | Danna et al. | 358/98 |
| B1 4,539,586 | 12/1991 | Danna et al. | 358/98 |
| 4,589,404 | 5/1986 | Barath et al. | 128/6 |
| 4,590,923 | 3/1986 | Watanabe | 128/6 |
| 4,611,888 | 9/1986 | Prenovitz et al. | 358/98 |
| 4,649,904 | 3/1987 | Kravter et al. | 128/6 |
| 4,651,202 | 3/1987 | Arakawa | 358/98 |
| 4,797,737 | 1/1989 | Yazawa | 358/98 |
| 4,853,773 | 8/1989 | Hibino et al. | 358/98 |
| 4,867,529 | 9/1989 | Utsumi et al. | 385/117 |
| 4,884,133 | 11/1989 | Kanno et al. | 358/98 |
| 4,901,142 | 2/1990 | Ikuno et al. | 358/98 |
| 4,920,413 | 4/1990 | Nakamura et al. | 358/98 |
| 4,924,856 | 5/1990 | Noguchi | 128/6 |
| 4,933,816 | 6/1990 | Hug et al. | 362/32 |
| 5,010,875 | 4/1991 | Kato | 128/6 |
| 5,042,915 | 8/1991 | Akustu et al. | 359/230 |
| 5,090,959 | 2/1992 | Samson et al. | 128/6 |
| 5,101,807 | 4/1992 | Kawashima | 128/6 |
| 5,134,469 | 7/1992 | Uchimura | 358/98 |
| 5,199,417 | 4/1993 | Muller et al. | 128/6 |
| 5,199,950 | 4/1993 | Schmitt et al. | 604/95 |

FOREIGN PATENT DOCUMENTS

| | | | |
|---|---|---|---|
| 0389453 | 9/1990 | European Pat. Off. | 128/6 |
| 0489937 | 6/1992 | European Pat. Off. | 604/95 |
| 4304530 | 8/1993 | Germany | 128/6 |

OTHER PUBLICATIONS

"CIS Myelocath" Brochure.

*Primary Examiner*—Richard J. Apley
*Assistant Examiner*—John Mulcahy
*Attorney, Agent, or Firm*—Bell, Seltzer, Park & Gibson

[57] ABSTRACT

A catheter imaging apparatus for internally viewing body vessels or cavities, having a catheter, the catheter comprising a housing of such a size as to be readily held in the hand of a user, an elongate tube with one end connected to the housing and extending outwardly therefrom and being formed of material having sufficient stiffness to maintain the elongate tube in a substantially straight condition in the absence of an external force applied thereto, the elongate tube having a flexible distal end portion, guide wires having inner ends connected to the housing and extending outwardly therefrom through the elongate tube means, distal ends of the guide wires being connected to the flexible distal end portion of the elongate tube means, and a guide wire control carried by the housing and cooperating with proximal inner end portions of the guide wires for controlling the angular attitude of the flexible distal end portion of the elongate tube means, the guide wires and guide wire control cooperating to limit the angular attitude of the flexible distal end portion of the elongate tube to angular adjustments in a common plane extending generally parallel to the upper surface of the housing, and an imaging source for forming an image of an internal body cavity or vessel into which the catheter is inserted, the imaging means being in optical communication with the flexible distal end portion of the elongate tube of the catheter.

9 Claims, 4 Drawing Sheets

CATHETER IMAGING APPARATUS

RELATED APPLICATIONS

This application is a continuation-in-part of U.S. Pat. application Ser. No. 07/908,403 filed on Jul. 6, 1992, and issued as U.S. Pat. No. 5,342,299, on Aug. 30, 1994.

FIELD OF THE INVENTION

This invention relates to medical catheters, and more particularly to a catheter imaging apparatus for creating images of body vessels or cavities.

BACKGROUND OF THE INVENTION

Recently, endoscopes have been extensively used whereby internal areas or organs within a body vessel or cavity may be observed by inserting an elongated insertable part of the endoscope through a catheter inserted into a body vessel or cavity, or directly into the body vessel or cavity itself. An endoscope, as used herein, is an instrument for examining the interior of a bodily canal or hollow organ. A catheter, on the other hand, is a tube inserted into a bodily channel, such as a vein, to distend or maintain an opening to a body vessel or cavity. Therapeutic treatments may be made by inserting surgical instruments or fluid through a treatment channel of the catheter. Various commercially available endoscopes and catheters exist for introducing into body vessels or cavities a variety of surgical tools, fluids, and other materials, such as radiographic contrast materials, angioplasty balloons, fiberoptic scopes, laser lights, and cutting instruments. Also, various techniques and systems have been developed for guiding or steering the catheters in the body vessels or cavities for use of these tools, fluids, and other materials.

In order to take pictures of an image observed by the endoscope or catheter and sent through an image guide such as the fiberoptic scope, a light source or imaging source apparatus must be included for adjusting exposure of an image within the body vessel or cavity. Various endoscope imaging systems have been used which supply a light source and a camera as separate devices for an imaging system. Examples of these separate devices in various systems may be seen in U.S. Pat. No. 5,134,469 by Uchimura entitled "*Endoscope Light Source Apparatus with Detachable Flash Unit*"; U.S. Pat. No. 5,101,807 by Kawashima entitled "*Endoscope Connecting Apparatus*"; U.S. Pat. No. 5,042,915 by Akutsu et al. entitled "*Light Source Apparatus For An Endoscope*"; U.S. Pat. No. 5,101,875 by Kato entitled "*Intravascular Endoscope Apparatus*"; U.S. Pat. No. 4,933,816 by Hug et al. entitled "*Inspection/Detection System With A Light Module For Use In Forensic Applications*"; U.S. Pat. No. 4,924,856 by Noguchi entitled "*Endoscope Light Source Apparatus*"; U.S. Pat. No. 4,920,413 by Nakamura et al. entitled "*Blood-Vessel Endoscope System for Storing Frozen Picture in Synchronization with Heart Pulsation*"; U.S. Pat. No. 4,901,142 by Ikuno et al. entitled "*Video Scope System*"; U.S. Pat. No. 4,884,133 by Kanno et al. entitled "*Endoscope Light Source Apparatus*"; U.S. Pat. No. 4,853,773 by Hibino et al. entitled "*Endoscope Signal Processing Apparatus Using Sequential and Synchronous Imaging Devices*"; U.S. Pat. No. 4,797,737 by Yazawa entitled "*Imaging Apparatus for Endoscope*"; U.S. Pat. No. 4,651,202 by Arakawa entitled "*Video Endoscope System*"; U.S. Pat. No. 4,539,586 by Danna et al. entitled "*Connector Module for Video Endoscopic System*"; U.S. Pat. No. B1 4,539,586 by Danna et al. entitled "*Connector Module for Video Endoscope System*"; U.S. Pat. No. 4,475,539 by Konomura entitled "*Endoscopic Television Apparatus*"; U.S. Pat. No. 4,344,092 by Miller entitled "*Miniature Video Camera Means for Video System*"; and U.S. Pat. Re. 33,854 by Adair entitled "*Rigid Video Endoscope With [Heat] Sterilization Sheath.*"

These separate systems, however, typically have the camera within an end of the endoscope itself which reduces the usefulness during surgical procedures because the physician typically has minimal control over the movement of the end of the endoscope. Also, these devices do not provide a catheter or other means for access to the body vessel or cavity while simultaneously viewing the vessel or cavity. Further, some of these devices provide a camera and a light source separate from the endoscope, but do not provide surgical access through a portion of the endoscope or a catheter and require control of two separate imaging sources which is awkward for a physician to handle during surgery because the physician needs to concentrate on the surgical procedure and not the operation of the separate imaging and light sources. Hence, additional personnel are often needed to control these various systems.

Other systems, such as seen in U.S. Pat. No. 4,589,404 by Barath et al. entitled "*Laser Endoscope*", provide the light source and camera in the same housing, but do not provide a catheter or endoscope for the system which allows the physician to access the body vessel or cavity for surgical purposes.

Therefore, there is still a need for a catheter imaging apparatus that allows for the control and manipulation of the catheter and imaging source while simultaneously using surgical tools, such as fiberoptic scopes or the like, and fluids needed for medical operations to thereby allow the physician to positionally locate, isolate, and view problem areas within the body vessel or cavity.

SUMMARY OF THE INVENTION

It is therefore an object of the present invention to provide a catheter imaging apparatus having catheter steering capability and freedom for viewing the internal body vessel or cavity.

These and other objects, features, and advantages of the present invention are provided in a catheter having more controlled movement in the distal end and having feedback on this movement to the catheter user, the details of which are disclosed in the detailed description and the enclosed drawings.

In accordance with the present invention, a catheter imaging apparatus for internally viewing body vessels or cavities is provided having a catheter, the catheter comprising a housing of such a size as to be readily held in the hand of a user, an elongate tube with one end connected to the housing and extending outwardly therefrom and being formed of material having sufficient stiffness to maintain the elongate tube in a substantially straight condition in the absence of an external force applied thereto, the elongate tube having a flexible outer end portion, guide wires having inner ends connected to the housing and extending outwardly therefrom through the elongate tube means, outer ends of the guide wires being connected to the flexible outer end portion of the elongate tube means, and a guide wire control carried by the housing and cooperating with inner end portions of the guide wires for controlling the angular attitude of the flexible outer end portion of the elongate tube means, the guide wires and guide wire control cooperating to limit the angular attitude of the flexible outer end portion of the elongate tube to angular adjustments in a common plane extending generally parallel to the upper surface of the housing and wherein the angular adjustment of the flexible outer end portion of the elongate tube means in all other planes is obtained by rotation of the user's hand, so that more control of the attitude of the flexible outer end portion of the elongate tube means is obtained during use of the catheter, and an imaging source for forming an image of an internal body cavity or vessel into which the catheter is inserted, the imaging means being in optical communication with the flexible outer end portion of the elongate tube of the catheter.

BRIEF DESCRIPTION OF THE DRAWINGS

Some of the objects and advantages of the present invention having been stated, others will become apparent as the description proceeds when taken in conjunction with the accompanying drawings, in which.

DESCRIPTION OF A PREFERRED EMBODIMENT

The present invention now will be described more fully hereinafter with reference to the accompanying drawings in which a preferred embodiment of the invention is shown. Like numbers refer to like elements throughout.

Figure 1:
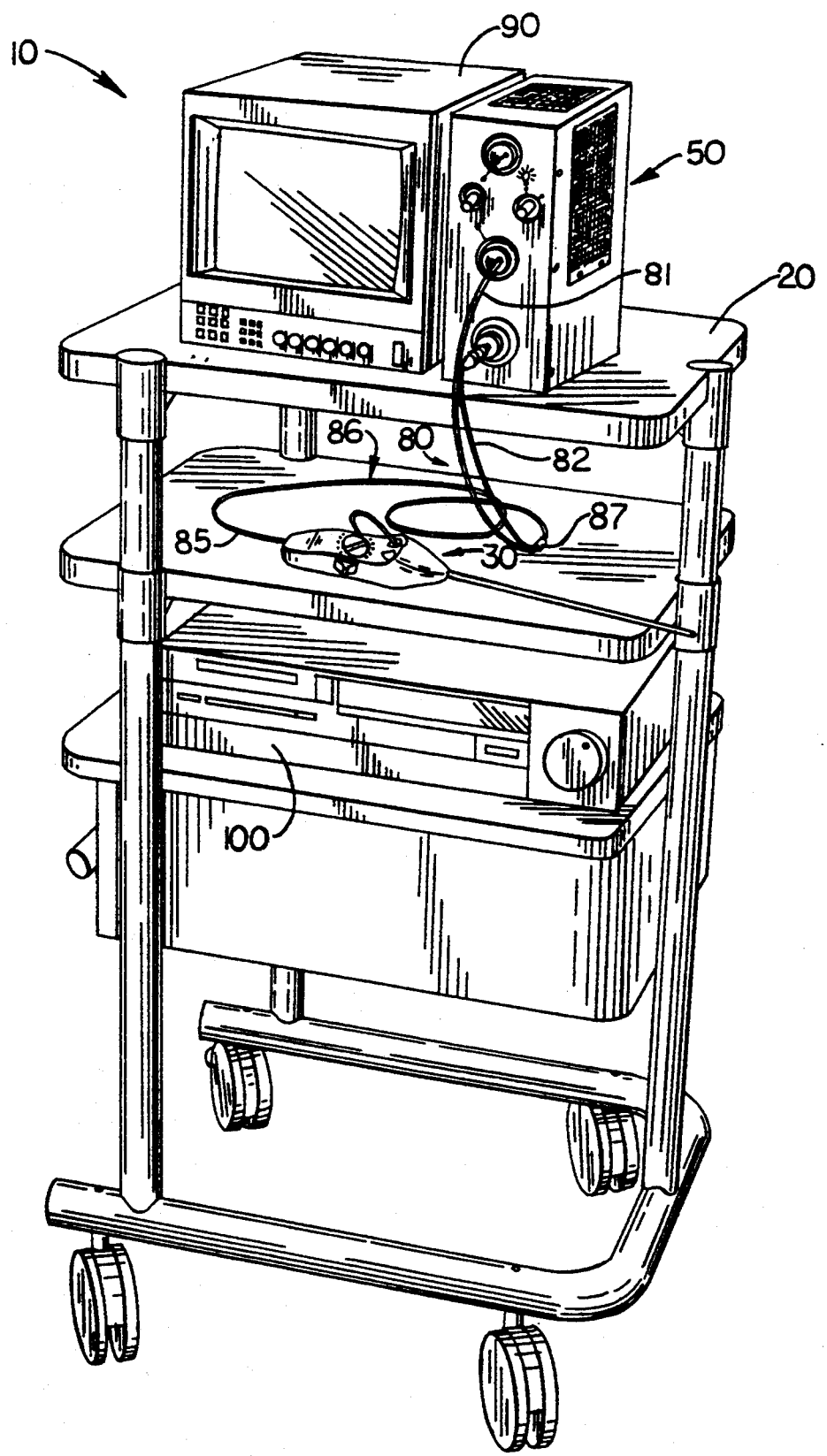
FIG. 1 is an environmental view of the catheter imaging apparatus according to a preferred embodiment of the present invention.

Referring now to FIG. 1, shown is an environmental view of a preferred embodiment of the catheter imaging apparatus 10 according to present invention for viewing portions of the human body such as vessel or cavities. It will also be understood by those skilled in the art that although the descriptions herein refer to use of the invention with humans, the catheter imaging apparatus 10, as disclosed herein and in the accompanying drawings, could be used for veterinary purposes or the like and thus are not limited to human use only. The catheter imaging apparatus 10 is portable as shown by the mounting cart 20 and has a catheter 30, an imaging source 50 communicating therewith, a cable assembly 80 communicating between the catheter 30 and the imaging source 50, an image display shown as a cathode ray tube ("CRT") 90 connected to the imaging source, and an image recorder shown as a video cassette recorder ("VCR") 100 connected to the image display. It will also be understood by those well skilled in the art that the image recorder 100 may be connected to the imaging source 50 for image recording as well as the image display 90.

Also, as shown in FIG. 1, the cable assembly 80 is typically a fiber optic cable and has a first end portion 81, a second end portion 82, and a third end portion 85. The first and second end portions 81, 82 attach to the imaging source 50 and the third end portion 85 enters an access port of the steerable catheter 30 for illuminating and detecting images from a body vessel or cavity. The first and second end portions 81, 82 also enter a common body portion 86 of the cable assemble 80 at a dual cable connector 87. The third end portion 85 then has a cable for providing illumination to the body vessel or cavity and a cable for detecting the image for the camera 61 (further shown in FIG. 4).

Figure 2:
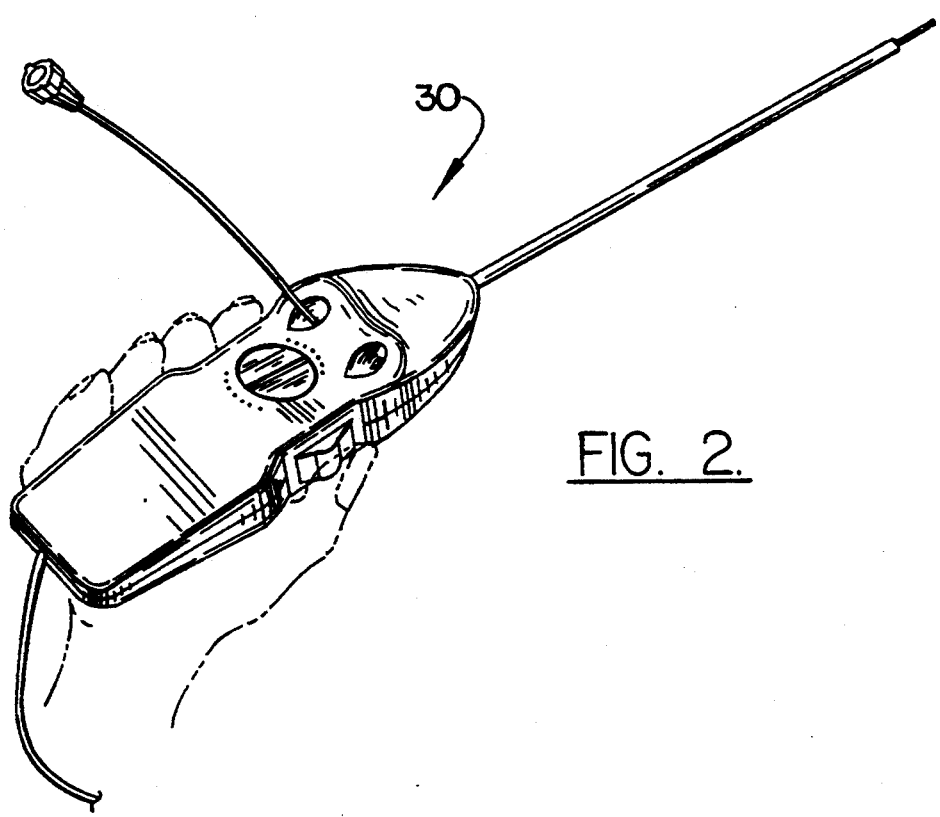
FIG. 2 is an environmental view of the steerable catheter being held in the hand of a user.

FIG. 2 is an environmental view of the steerable catheter 30 being held in the hands of a user. The steerable catheter 30 was disclosed and described in U.S. patent application Ser. No. 07/908,403 filed on Jul. 6, 1992 (now U.S. Pat. No. 5,342,299) which is hereby incorporated herein by reference. As such, further details of the steerable catheter 30 will not be discussed except for improvements to the catheter disclosed herein.

As described in copending U.S. patent application Ser. No. 07/908,403, the steerable catheter 30 has control wires extending from the housing through an elongate tube. These control wires may form one continuous wire in the elongate tube instead of two or more wires. Also, a thin-walled semi-rigid tube may be inserted within a portion of either of the lumens within the elongate tube to provide further rigidity and still allow flexibility in the distal end portion thereof. The lumens may have similar diameters or may have diameters of different sizes. Further, it will be recognized by those well skilled in the art to use various connecting configurations of the guide wires extending from the elongate tube into the housing. The guide wires may be connected to the control wheel or an interior portion of the housing. The interfacing configuration of the guide wires with the control wheel may also vary to still provide flexible steering and control of the distal end of the elongate tube. Finally, as shown in FIG. 1, the proximal tube extending from the housing may also be used for inserting a fiberscope or the like therein since the tube extends into a lumen of the elongate tube. The fluid port, in this embodiment, could be formed by one of the access ports in the housing.

Figure 3:
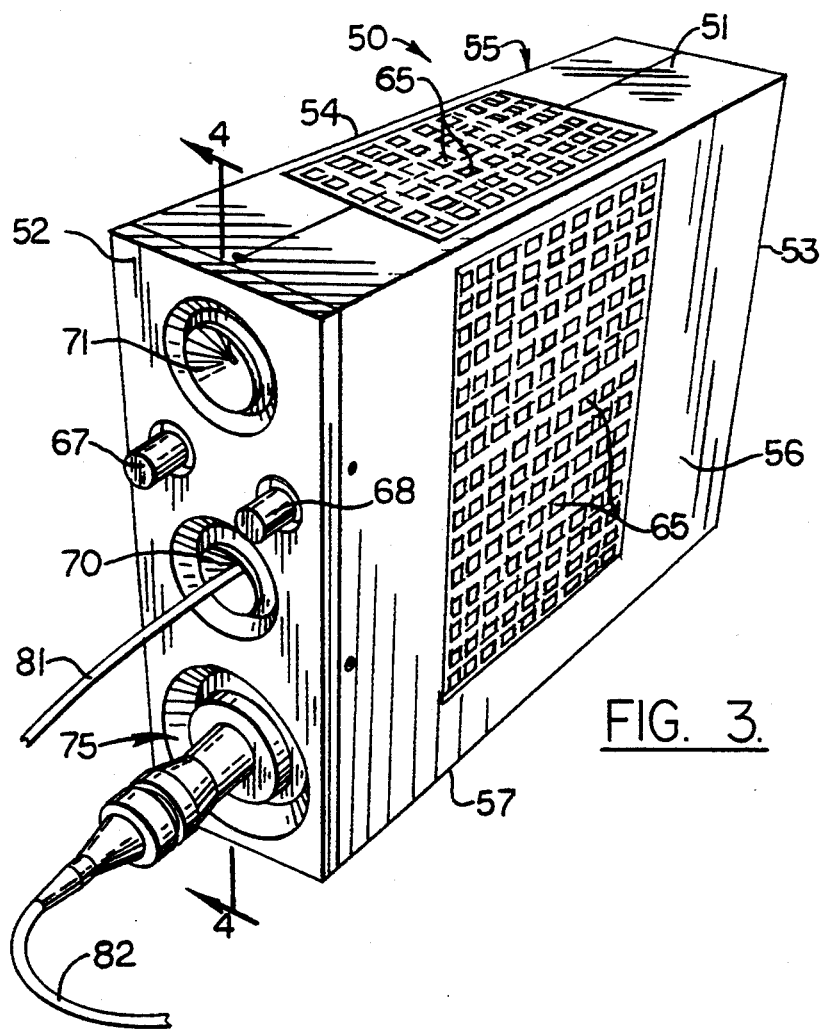
FIG. 3 is a perspective view of the imaging source of the catheter imaging apparatus according to the present invention.
Figure 4:
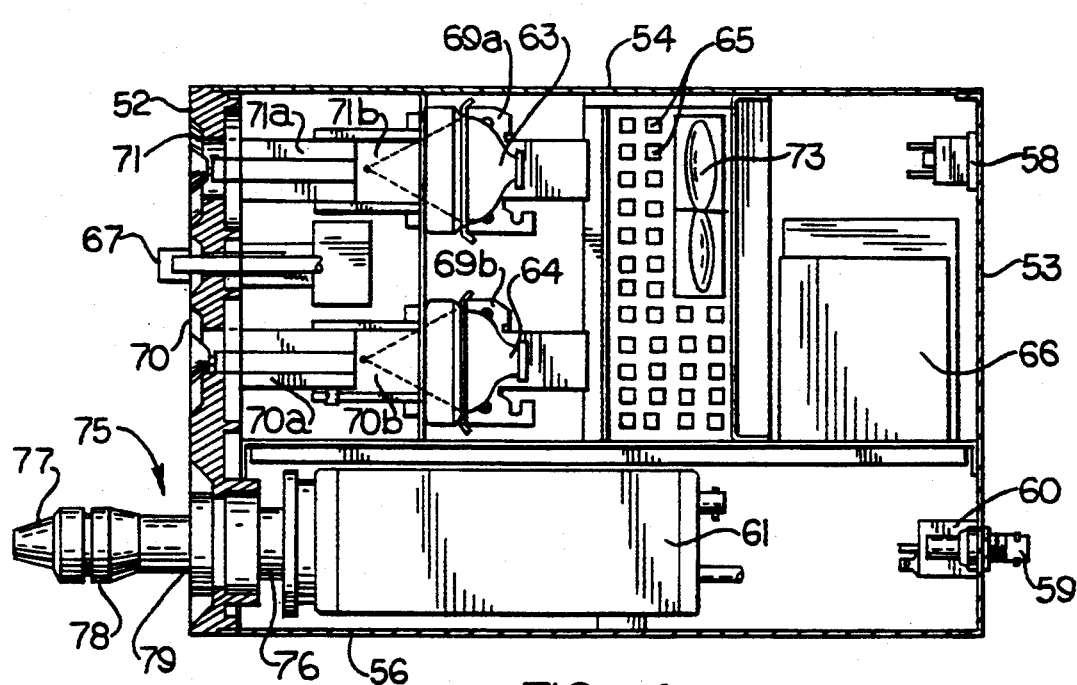
FIG. 4 is a side cross-sectional view of the imaging source according to the present invention taken along line 4—4 of FIG. 3.

FIGS. 3-6 further disclose the construction of the imaging means shown as the imaging source 50 according to the present invention. FIG. 3 is a perspective view of the imaging source 50 of the catheter imaging apparatus 10. FIG. 4 is a cross-sectional view of the imaging source 50 taken along line 4—4 in FIG. 3. The imaging source 50 has a housing 51 in the shape of a rectangular box having various ends shown as front panel 52 and a back panel 53, and various sides shown as side panels 54, 55, 56, and 57 respectively. The housing 51 of the imaging source 50 has an image detector shown as a video camera 61, an image illuminating means shown as light sources 63, 64 mounted in a light guide brackets 69a, 69b, a power supply shown as a transformer 66, and illumination control means shown as control knobs 67, 68, in the form of a rheostat and a switch, for controlling the light sources 63, 64. The light sources 63, 64 are typically luminescent lamps, but may comprise various other light sources well known to those skilled in the art such as laser diodes or the like.

The back panel 53 shown in FIG. 4, has various connectors 58, 59, 60 for interfacing and communicating with the CRT 90 and/or the VCR 100. Connector 58 provides connection for power to the imaging source 50, connector 59 provides connection to the VCR 100 for recording the image produced by the video camera 61, and connector 60 provides connection to the CRT 90 for viewing the image produced by the video camera 61. Various air vents 65 are located in the side panels 54, 55, 56 to provide ventilation and cooling for the light sources 63, 64. The air vents 65 may also be located in the back panel 53 (not shown in the drawings). The fan 73 also provides cooling for the imaging source 50.

Figure 6:
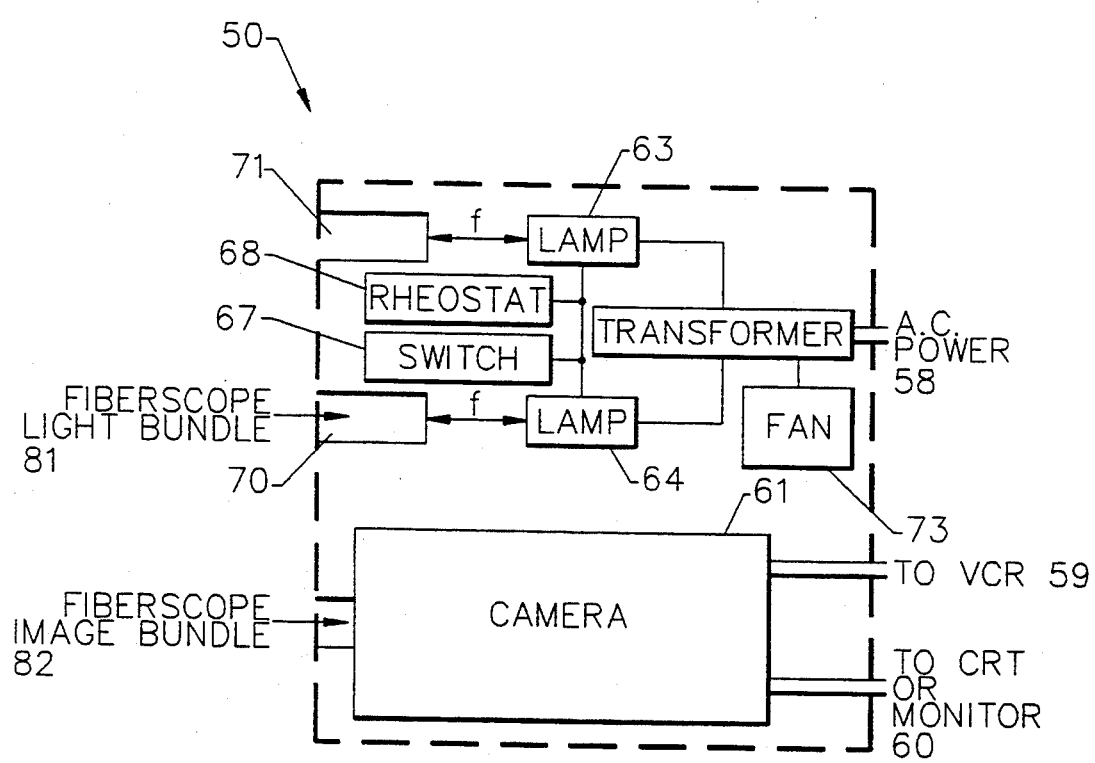
FIG. 6 is a schematic block diagram of the imaging source according to the present invention.

The front panel 52 has image illuminating connectors 70 or 71 in spaced apart relation to each other and to the control knobs 67, 68. The image illuminating connectors 70, 71 provide connection for a first end portion 81 of the cable assembly 80. The first end portion 81 may be connected to either connector 70 or 71. The illuminating connectors 70, 71 include respective focusing collet assemblies which have adjusting rings 70a, 71a and bases 70b, 71b. The focusing collet assemblies focus the light from the light sources 63, 64 into the cable assembly 80. The focal point, designated f as shown in FIG. 6, is determined by the luminescent lamp of the light source and adjusted by the focusing collet assembly. The two light sources 63, 64 and the two connectors 70, 71 provide a redundant illuminating means to thereby reduce illuminating failure problems during surgery. If one light source fails, the first end portion 81 of the cable assembly 80 may be switched to the other light source. Control knob 67 provides a switching means between the light sources 63, 64 and control knob 68 provides control of the amount of illumination provided to the cable assembly 80 and thereby to the body vessel or cavity. The front panel 52 also has an image control connector 75 connected to the camera 61 within the housing 51 on one end 76 and for attachment of a second end portion 82 of the cable assembly 80 at the other end 77 as discussed above with reference to FIG. 1.

Figure 5:
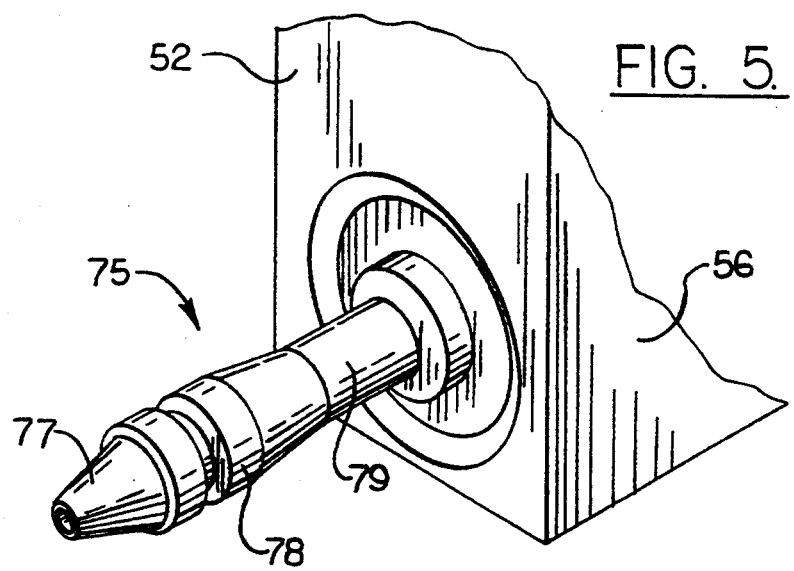
FIG. 5 is an enlarged perspective view of the image control connector of the imaging source according to the present invention.

FIG. 5 is an enlarged perspective view of the image control connector 75 according to the present invention to further describe its construction and operation. The end 77 of the image control connector 75 is tapered from a central body portion 78 to provide ease of connection to the second end portion 82 of the cable assembly 80. The image control connector further has an image control knob 79 along the medial body portion 78 toward end 76. The image control knob 79 allows the user or physician to control camera imaging, and particularly such as zoom lens capability as illustrated. The camera imaging may also comprise focus, vertical or horizontal adjustments, zoom lens capability, and other camera imaging control well known to those skilled in the art.

FIG., 6 is a schematic block diagram of the imaging source 50 according to the present invention. The block diagram further illustrates the internal components of the imaging source 50 and the redundant imaging light sources 63, 64.

In the drawings and specification, there have been disclosed typical preferred embodiments of the invention and, although specific terms are employed, they are used in a generic and descriptive sense only and not for the purposes of limitation, the scope of the invention being set forth in the following claims.

That which is claimed is:

1. A catheter imaging apparatus for internally viewing body vessels or cavities, comprising:

a catheter comprising:
   a catheter housing having an upper surface and a lower surface and being of such a size as to be readily held in the hand of a user,
   elongate tube means having a proximal end connected to said housing and extending outwardly therefrom and being formed of a material having sufficient stiffness to maintain said elongate tube means in a substantially straight condition in the absence of an external force applied thereto, said elongate tube means having a flexible distal end portion and at least one lumen longitudinally extending from said distal end portion to said proximal end,
   an access port positioned within said upper surface of said catheter housing for accessing said lumen of said elongate tube means,
   means positioned within said catheter housing for connecting said access port to said lumen of said elongate tube means,
   guide wires having proximal ends positioned within and connected to said housing and extending outwardly therefrom through said elongate tube means, distal ends of said guide wires being connected to said flexible distal end portion of said elongate tube means,
   guide wire control means carried by said housing and cooperating with proximal end portions of said guide wires for controlling the angular attitude of said flexible distal end portion of said elongate tube means, said guide wires and control means cooperating to limit the angular attitude of said flexible distal end portion of said elongate tube means to angular adjustments in a common plane extending generally parallel to said upper surface of said catheter housing and wherein the angular adjustment of said flexible distal end portion of said elongate tube means in all other planes is obtained by rotation of a user's hand so that more control of the attitude of said flexible distal end portion of the elongate tube means is obtained during use of the catheter, and
   a central axis extending longitudinally from said flexible distal end portion of said elongate tube means, through said elongate tube means, and into said housing, and wherein said control means comprises a rotating control wheel connected to said proximal ends of said two of said guide wires so that rotation of said control wheel guides the flexible distal end portion of said elongate tube means in an angular attitude from said longitudinally extending central axis in a generally transverse direction therefrom; and
imaging means for forming an image of an internal body cavity or vessel into which said catheter is inserted, said imaging means being in optical communication with said flexible distal end portion of said elongate tube means of said catheter through said access port in said upper surface of said catheter housing and through said lumen of said elongate tube means.

2. A catheter imaging apparatus according to claim 1, wherein said imaging means comprises:

an imaging housing including front and back surfaces;
illuminating means positioned within said imaging housing for internally illuminating a body vessel or cavity for viewing, said illuminating means being in optical communication with said catheter through said front surface of said imaging housing and comprising a luminescent lamp; and detecting means positioned within said imaging housing closely adjacent said illuminating means for detecting images of a body vessel or cavity from said catheter that are illuminated by said illuminating means, said detecting means being in optical communication with said catheter through said front surface of said imaging housing and comprising a video camera.

3. A catheter imaging apparatus according to claim 2, wherein said imaging means further comprises a focusing collet assembly cooperating with said luminescent lamp and adapted to focus light transmitted by said luminescent lamp to said flexible distal end portion of said catheter.

4. A catheter imaging apparatus according to claim 2, and further comprising a fiber optic cable assembly adapted to be inserted within one of said at least one lumens of said catheter through said access port in said upper surface of said catheter housing and to connect to said imaging means for providing optical communication between said catheter and said imaging means.

5. A catheter imaging apparatus according to claim 4, wherein said cable assembly has one end portion be inserted adapted to insert within said lumens through said access port in said upper surface of said catheter and another end portion adapted to connect to said illuminating means and said detecting means, through said front surface of said imaging housing of said imaging means.

6. A catheter imaging apparatus according to claim 1, wherein said catheter further comprises a pair of access ports positioned within an upper surface of said housing and wherein said at least one lumen of said elongate tube means of said catheter comprises two lumens extending longitudinally through said elongate tube means, through said housing, and to said access ports.

7. A catheter imaging apparatus according to claim 6, wherein one of said lumens extending longitudinally through said elongate tube means has a larger diameter than the other lumens extending longitudinally through said elongate tube means.

8. A catheter imaging apparatus according to claim 1, further comprising image display means communicating with said imaging means for displaying the image formed by said imaging means.

9. A catheter imaging apparatus according to claim 1, further comprising image recording means communicating with said imaging means for recording an image formed by said imaging means.

* * * * *

UNITED STATES PATENT AND TRADEMARK OFFICE
CERTIFICATE OF CORRECTION

PATENT NO.  : 5,423,311

DATED       : June 13, 1995

INVENTOR(S) : Snoke et al.

It is certified that error appears in the above-identified patent and that said Letters Patent is hereby corrected as shown below:

Column 6, line 48, "said", (first occurrence) should be deleted.

Column 7, lines 25-26, "be inserted" should be deleted.

Column 7, line 26, "insert" should be --be inserted--.

Signed and Sealed this

Tenth Day of October, 1995

Attest:

BRUCE LEHMAN

Attesting Officer

Commissioner of Patents and Trademarks